(12) United States Patent
Roane

(10) Patent No.: US 6,171,108 B1
(45) Date of Patent: Jan. 9, 2001

(54) ENDODONTIC FILE HANDPIECE

(76) Inventor: James B. Roane, 11609 E. State Highway 9, Norman, OK (US) 73026

(*) Notice: Under 35 U.S.C. 154(b), the term of this patent shall be extended for 0 days.

(21) Appl. No.: 09/313,567

(22) Filed: May 12, 1999

(51) Int. Cl.[7] ........................... A61C 5/02
(52) U.S. Cl. ............... 433/224; 433/102; 433/114
(58) Field of Search ................... 433/102, 114, 433/125, 130, 224

(56) References Cited

U.S. PATENT DOCUMENTS

| | | |
|---|---|---|
| 1,694,857 | 12/1928 | Kulik . |
| 3,578,745 | 5/1971 | Garnier . |
| 3,713,221 | 1/1973 | Malmin . |
| 3,969,823 | 7/1976 | Nakanishi . |
| 4,243,388 | 1/1981 | Arai ........................ 433/27 |
| 4,443,193 | 4/1984 | Roane ...................... 433/102 |
| 4,629,426 | 12/1986 | Levy ........................ 433/118 |
| 4,940,410 | 7/1990 | Apap et al. ............... 433/102 |
| 5,586,886 | 12/1996 | Roane ...................... 433/224 |
| 5,735,689 | * 4/1998 | McSpadden ............. 433/102 |

FOREIGN PATENT DOCUMENTS

| | | |
|---|---|---|
| 207037 | 1/1960 | (AT) . |
| 497996 | 5/1930 | (DE) . |
| 2616652 | 12/1988 | (FR) . |

OTHER PUBLICATIONS

Nakanishi Dental Mfg. Co., Ltd., *Clinical & Laboratory Rotary Cutting Instruments*, pp. 4–9, printed in Australia, Dec. 21, 1993.

* cited by examiner

Primary Examiner—Ralph A. Lewis
(74) Attorney, Agent, or Firm—C. Clark Dougherty, Jr.

(57) ABSTRACT

An improved rotary handpiece and endodontic file for cleaning and enlarging a root canal of a tooth are provided by the present invention. The handpiece includes a rotary drive connected to a chuck assembly for rotating the endodontic file and a movable latch assembly for holding the endodontic file while allowing the chuck assembly to rotate the file about its axis. Means for moving the latch assembly towards and away from the chuck assembly at controlled rates and thereby advancing and retracting the endodontic file at controlled rates are attached to the handpiece and to the latch assembly.

20 Claims, 3 Drawing Sheets

ENDODONTIC FILE HANDPIECE

BACKGROUND OF THE INVENTION

1. Field of the Invention

The present invention relates to an improved rotary handpiece and an endodontic file for use therewith whereby the endodontic file can be advanced, retracted and rotated at controlled rates.

2. Description of the Prior Art

Endodontics is the branch of dentistry which involves the treatment of pulp through root canal therapy. Such therapy generally includes the cleaning of the root canal to remove damaged tissue therefrom and to enlarge the root canal so that it can be filled with an inert sealing material, e.g., gutta-percha. Typically, a dentist will drill into the upper part of the tooth to locate the root canal and thereafter clean and enlarge the root canal using small endodontic instruments, generally referred to in the art as "files."

The cleaning and enlarging of a root canal is complicated by the fact that the root canal is not only very small, but often follows a curved path. Accordingly, the file must be very thin and flexible in order to enter the root canal and follow its path. Also, the file must have sufficient strength so that it is not easily broken off within the root canal. A particularly suitable endodontic file which readily follows the paths of root canals is the K-type file disclosed in my U.S. Pat. No. 4,443,193 issued on Apr. 17, 1984. As described in detail in the patent, the inventive K-type file includes a tapered working portion defined on a flexible shaft. The working portion includes three spiral rotationally bi-directional cutting edges formed thereon. A tapered tip is formed on the flexible shaft which intersects the ends of the cutting edges on the working portion of the file. The tapered tip is shaped such that sharp cutting points at the intersections between the ends of the cutting edges and the tip are eliminated so that lateral transportation of the instrument when cutting a curved root canal is also eliminated. The file can be formed of various materials including, but not limited to, stainless steel or a nickel titanium alloy.

Heretofore, the most common procedure followed by dentists in performing root canals has been to utilize hand manipulated K-type files of progressively increasing size. When a K-type file is manipulated by hand to clean and enlarge a root canal, a number of types of cutting strokes can be utilized which generally fall into the categories of filing or reaming. A filing stroke utilizes axial reciprocation of the cutting instrument along the length of the root canal without rotating the instrument. Thus, the edges of a K-type instrument cut the interior walls of the root canal when a filing stroke is used therewith. A reaming stroke refers to the use of rotational motion established by rotating the instrument about its longitudinal axis. While there are various kinds of instruments, some of which cut in a single rotational direction, K-type files have spiral edges which are rotationally bi-directional in that they cut when rotated either clockwise or counterclockwise. The spiral cutting edges are generally right-handed whereby when a K-type file is rotated clockwise it tends to thread itself into the root canal like a wood screw. Thus, the dentist must be careful not to penetrate too deeply into the root canal as a result of self-threading which can damage the tooth and subject the file to excessive loading.

A variety of dental instrument drive devices, known in the art as "handpieces," have been developed for rotating dental instruments. While the use of rotary handpiece driven endodontic files has achieved some degree of success, a continuing problem involves the self-threading of the endodontic file into the canal whereby the file penetrates the canal too rapidly and becomes excessively loaded. Such excessive stress on the instrument driven by a handpiece can result in sticking or breaking of the instrument in the canal, a condition which is difficult to correct.

An improved rotary handpiece and methods of cleaning and enlarging a root canal of a tooth utilizing the handpiece and a rotary endodontic file are described in my U.S. Pat. No. 5,586,886 issued on Dec. 24, 1996. As described in the patent, the improved handpiece basically comprises a rotary drive which rotates a chuck for holding and rotating the endodontic file. A retractable support rod is attached to and extends from the handpiece positioned adjacent and substantially parallel to the endodontic file. The support rod is adapted to rest on a tooth whereby the retraction of the support rod controls the advance of the endodontic file into the root canal. Means are attached to the handpiece and to the support rod for retracting the support rod and advancing the endodontic file at a controlled rate into the root canal whereby the endodontic file does not become excessively loaded while the root canal is being cleaned and enlarged. While this patented handpiece constitutes a distinct improvement over prior art endodontic file handpieces which do not control the rate of advance of the endodontic file into a root canal, it has the disadvantage that it is more difficult for a dentist using the handpiece to see the file as it is being fed into or out of a root canal and to feel the progress or non-progress of the file in cleaning and enlarging the root canal. Further, the patented handpiece design depends upon the presence of sound tooth structure beneath the support rod and thus, it can limit the freedom of position needed to accomplish root canal treatments and reduce the full positioning ability sometimes required in clinical situations.

Thus, there is a continuing need for an improved rotary handpiece for cleaning and enlarging a root canal of a tooth with a rotary endodontic file which prevents the file from becoming excessively loaded whereby it sticks or breaks off in the canal.

SUMMARY OF THE INVENTION

The present invention provides an improved rotary handpiece and a rotary endodontic file for use therewith as well as methods of cleaning and enlarging a root canal of a tooth utilizing the handpiece and the rotary endodontic file which meet the needs described above and overcome the deficiencies of the prior art. The improved handpiece of the invention basically comprises a rotary drive connected to a chuck assembly for rotating an endodontic file disposed therein. A latch assembly for holding the endodontic file, while allowing the chuck assembly to rotate the file about its axis is movably attached to the handpiece and positioned adjacent to the chuck assembly. When the handpiece and the endodontic file held thereby are positioned so that the file will enter a root canal and the latch assembly is moved towards or away from the chuck assembly, the endodontic file is advanced into or retracted from the root canal. Means are attached to the handpiece and to the latch assembly for moving the latch assembly toward and away from the chuck assembly and thereby advancing and retracting the endodontic file at a controlled rate so that the file does not become excessively loaded while the root canal is being cleaned and enlarged.

The rotary endodontic file provided by this invention is comprised of a flexible shaft having a plurality of cutting edges formed thereon and having a handle attached thereto.

The handle includes an elongated portion having the cross-sectional shape of a straight line segment of a circle and having a peripheral circular groove formed therein.

The methods of this invention for cleaning and enlarging a root canal of a tooth utilizing the improved handpiece and rotary endodontic file basically comprise latching the endodontic file to the handpiece which has a chuck assembly for rotating the file and a latch assembly for holding the file while allowing the chuck assembly to rotate the file about its axis, the latch assembly being selectively movable towards or away from the chuck assembly whereby the file is advanced or retracted. The handpiece is then positioned with the endodontic file positioned to enter the root canal, the endodontic file is rotated and the endodontic file is advanced into and retracted from the root canal in a manner and at controlled rates whereby the file does not become excessively loaded while the root canal is being cleaned and enlarged.

It is, therefore, a principal object of the present invention to provide an improved rotary handpiece and a rotary endodontic file for use therewith as well as methods for cleaning and enlarging the root canals of teeth using the improved handpiece and rotary endodontic file.

Other and further objects, features and advantages of the present invention will be readily apparent to those skilled in the art upon a reading of the description of preferred embodiments which follows when taken in conjunction with the accompanying drawings.

DESCRIPTION OF THE PREFERRED EMBODIMENTS

Figure 1:
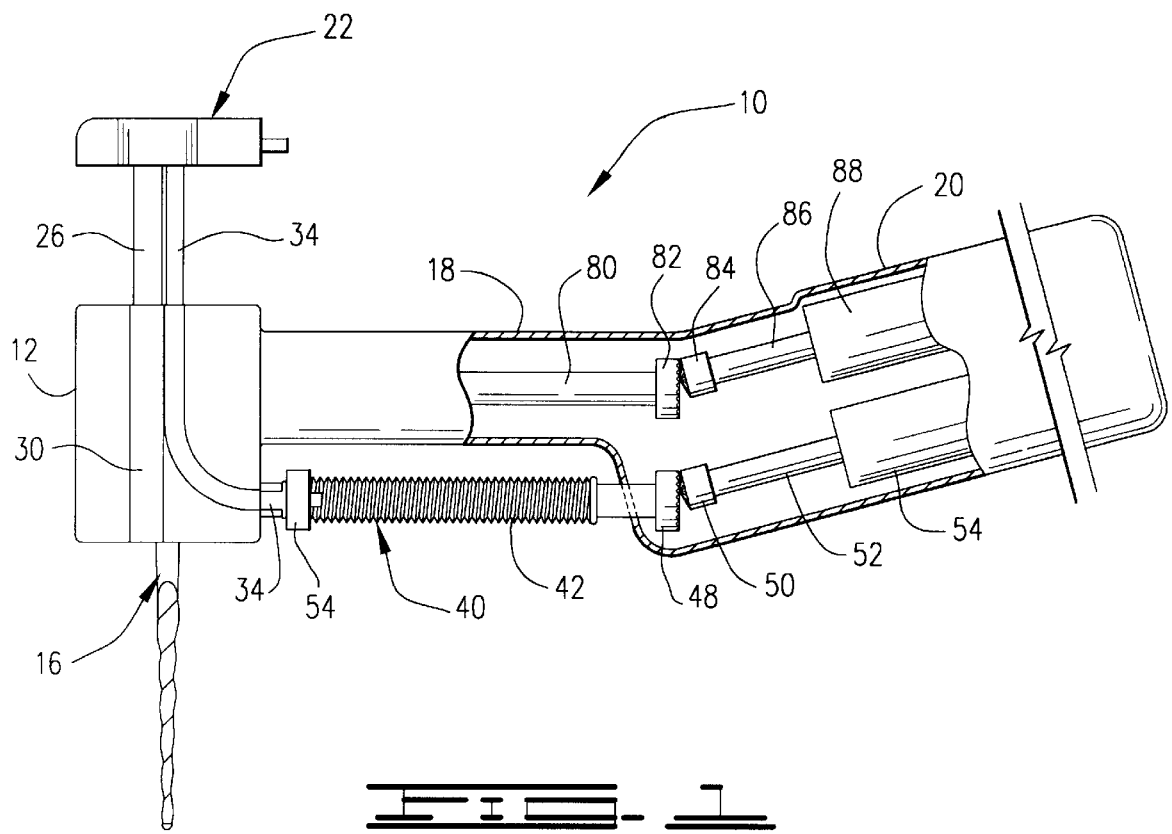
FIG. 1 is a side partially cutaway view of a rotary handpiece of the present invention having an endodontic file of the invention latched thereto.
Figures 2, 3:
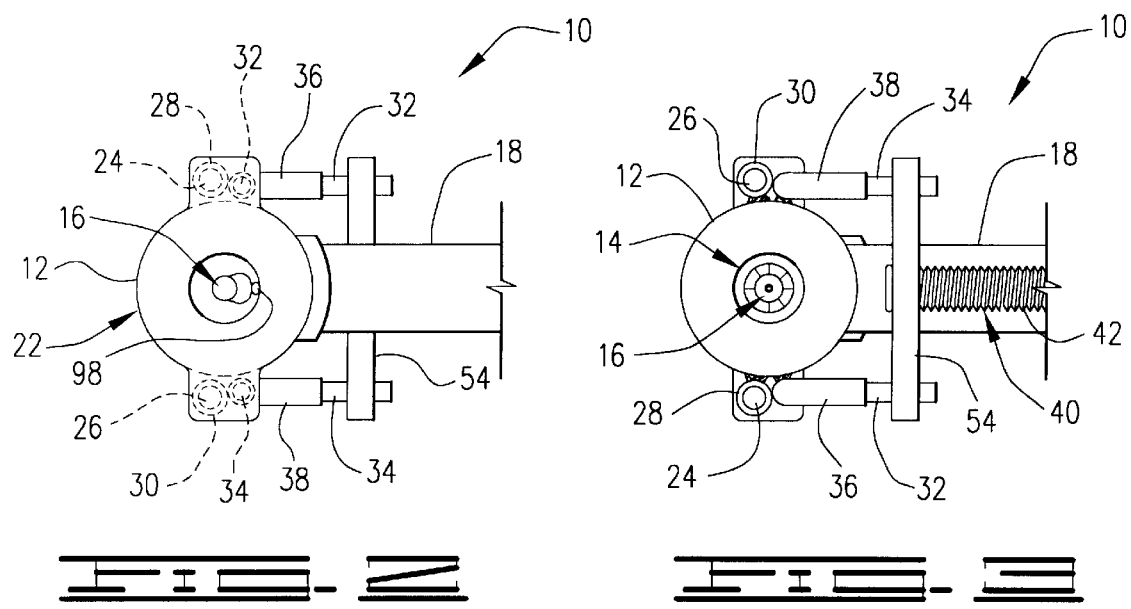
FIG. 2 is a partial top view of the handpiece and endodontic file of FIG. 1.
FIG. 3 is a partial bottom view of the handpiece and endodontic file of FIG. 1.

As mentioned, an improved K-type endodontic file is described in my U.S. Pat. No. 4,443,193 issued Apr. 17, 1984. The improved file includes a flexible shaft having a tapered working portion thereon. A plurality of spiral rotationally bi-directional cutting edges are formed on the working portion and a non-ledging tapered tip shaped such that the sharp cutting points which are normally present in a K-type file at the intersections between the ends of the cutting edges and a standard 75° (plus or minus 15°) included angle conically tapered tip are substantially eliminated. By eliminating the sharp points, the high stress concentrations previously created when the points engage tooth material in a curved root canal are eliminated. That is, the forces exerted by the axially most forward part of the improved file against the wall of a curved root canal is spread over a much greater area of the tooth material and transportation of the instrument and ledging of the canal are eliminated or reduced.

Prior to the present invention, my above described improved K-type file and other types of endodontic files were most commonly hand manipulated to minimize self-threading, excessive loading of the files and sticking or breaking of the files as was often the case when an endodontic file driven by a conventional rotational handpiece was used. The present invention provides an improved rotary handpiece and an endodontic file for use therewith which solve the above mentioned problems and insure that the endodontic file does not self thread or otherwise become excessively loaded while a root canal is being cleaned and enlarged.

Referring now to the drawings, and particularly to FIGS. 1–5, the improved rotational handpiece and endodontic file of the present invention are illustrated and generally designated by the numeral 10. The handpiece 10 is basically comprised of a head portion 12 having an internal rotating chuck assembly 14 for rotating the endodontic file 16 disposed therewithin connected by a shank portion 18 to a rotary drive portion 20.

A latch assembly 22 for holding the endodontic file 16 while allowing the chuck assembly 14 to rotate the file 16 about its axis is movably attached to the head portion 12 of the handpiece 10. The latch assembly 22 is positioned adjacent to the head portion 12 and is movably attached to the head portion 12 by a pair of guide rods 24 and 26 attached to opposite sides of the latch assembly 22. The guide rods 24 and 26 are slidably disposed within a pair of guide tubes 28 and 30 which are attached to opposite sides of the head portion 12.

Figure 4:
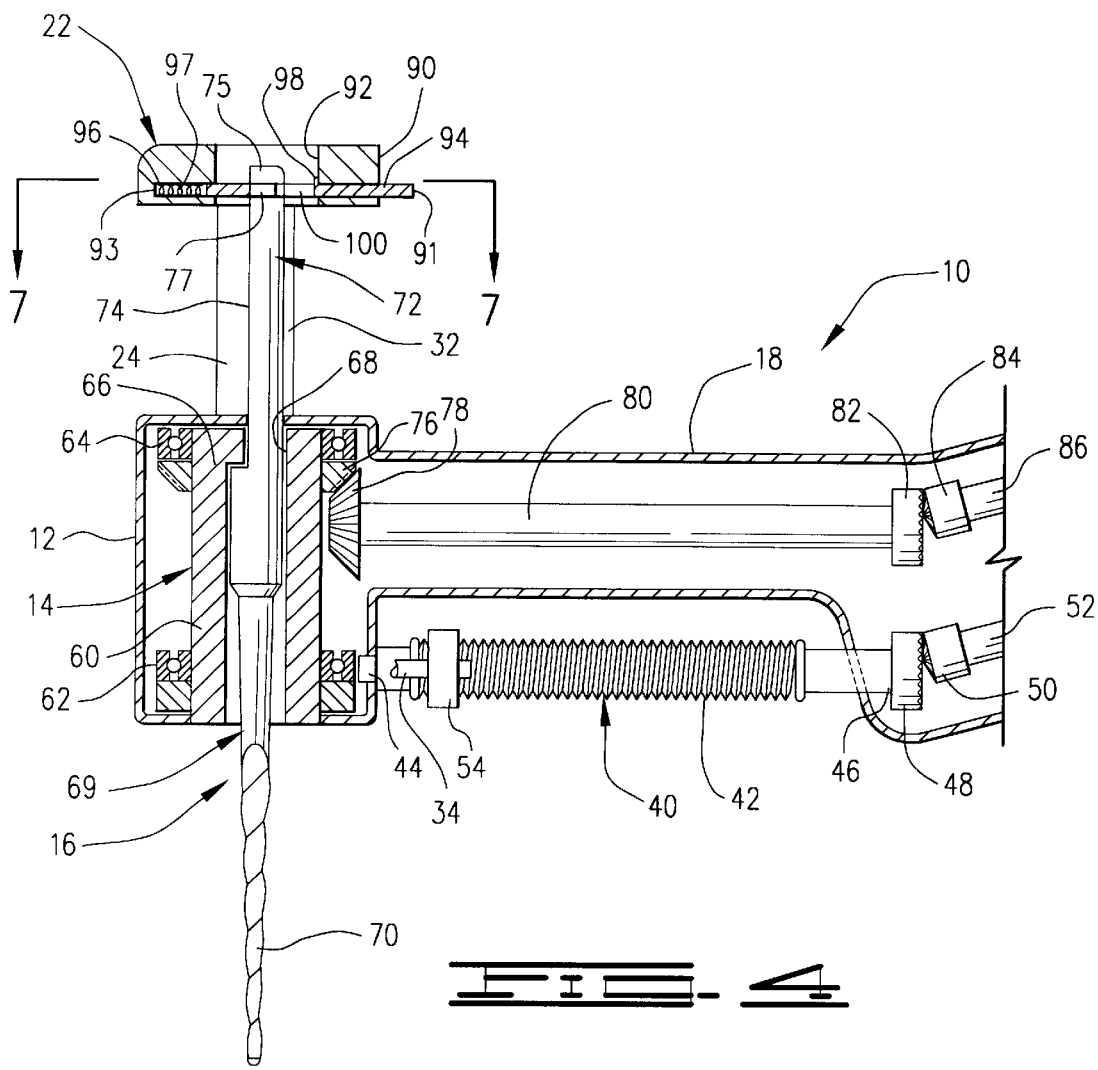
FIG. 4 is an enlarged side cross-sectional view of the forward portion of the handpiece of FIG. 1 showing a side view of the endodontic file and showing the latch assembly and endodontic file in the fully retracted position.
Figure 5:
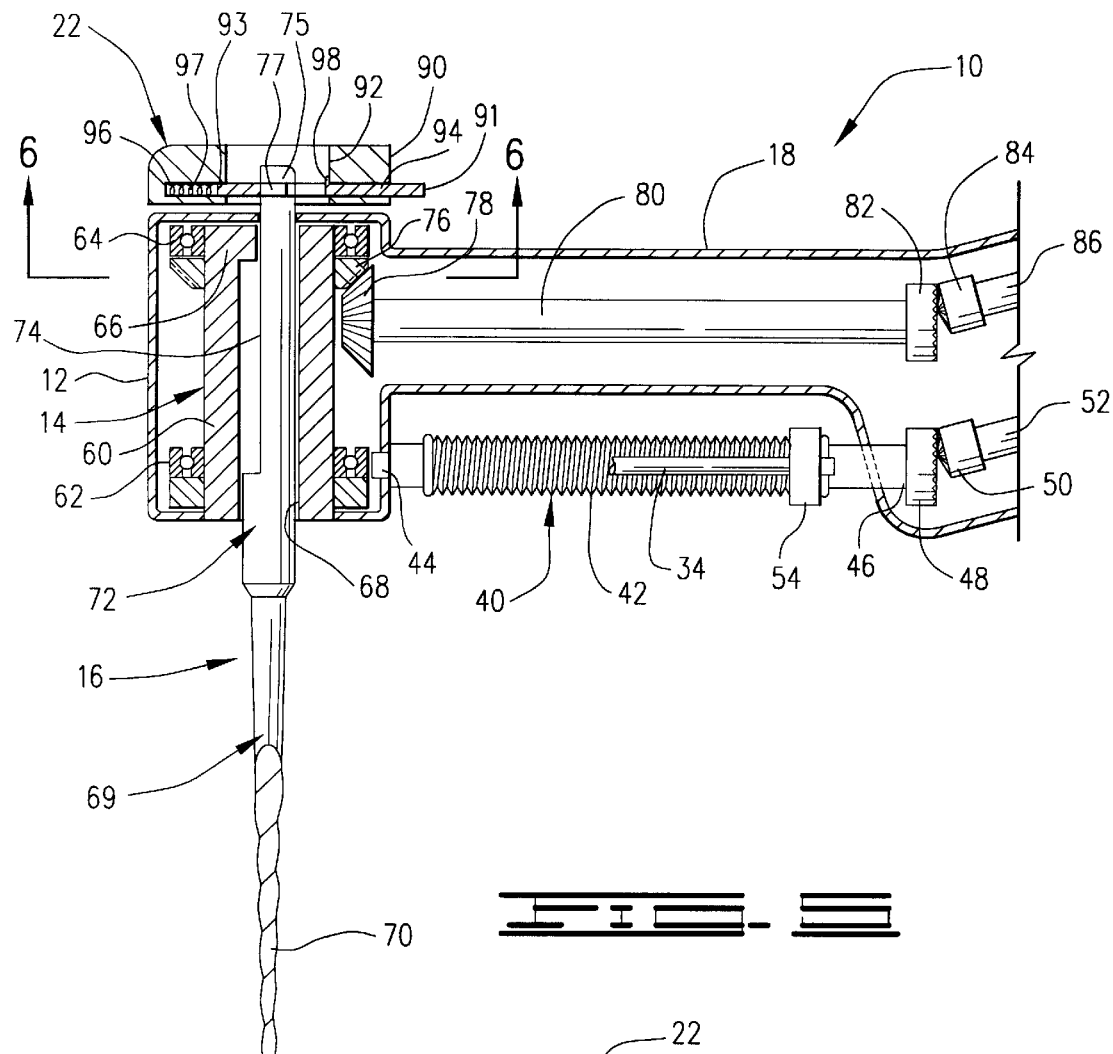
FIG. 5 is an enlarged side cross-sectional view similar to FIG. 4, but showing the latch assembly and endodontic file in the fully advanced position.

The latch assembly 22 is movable from a position immediately adjacent to the chuck assembly 14 as shown in FIG. 5 to a position away from the chuck assembly 14 as shown in FIGS. 1 and 4. When the latch assembly 22 is in the position adjacent to the chuck assembly 14 shown in FIG. 5, the endodontic file 16 is fully advanced as is also shown in FIG. 5. When the latch assembly 22 is in the position away from the chuck assembly 22 shown in FIGS. 1 and 4, the endodontic file 16 is fully retracted as is also shown in FIGS. 1 and 4.

A pair of flexible rods 32 and 34 are attached to the latch assembly 22 for pulling the latch assembly 22 towards the chuck assembly 14 and pushing the latch assembly 22 away from the chuck assembly 14. As shown best in FIGS. 1–3, the flexible rods 32 and 34 extend through a pair of curved guide tubes 36 and 38 attached to opposite sides of the head portion 12. The other ends of the flexible rods 32 and 34 are connected to a longitudinal drive assembly generally designated by the numeral 40 for pulling and pushing the rods.

The longitudinal drive assembly 40 includes a threaded shaft 42 which is rotatably journaled at its forward end 44 to the head portion 12 of the handpiece 10. The rearward end 46 of the threaded shaft 42 is journaled to the rotary drive portion 20 of the handpiece 10 and is connected to a drive gear 48. As shown best in FIG. 1, the drive gear 48 is in engagement with a beveled gear 50 which is connected to the drive shaft 52 of a rotary drive 54, e.g., a reversible electric or air drive motor. An elongated threaded follower 54 is threadedly engaged on the threaded shaft 42. The ends of the threaded follower 54 are attached to the flexible rods 32 and 34. As will now be understood by those skilled in the art, the threaded follower 54 moves longitudinally on the shaft 42 when the shaft is rotated by the rotary drive 54. When the shaft 42 is rotated in a clockwise direction, the latch assembly 22 is moved toward the chuck assembly 14 thereby advancing the endodontic file 16 and when the shaft 42 is rotated in a counterclockwise direction, the latch assembly 22 is moved away from the chuck assembly 14 thereby retracting the endodontic file 16. As will be understood by those skilled in the art, the above description assumes the shaft 42 has right hand threads. If the shaft 42 has left hand threads, the opposite shaft rotations will move the latch assembly as described above.

Figure 6:
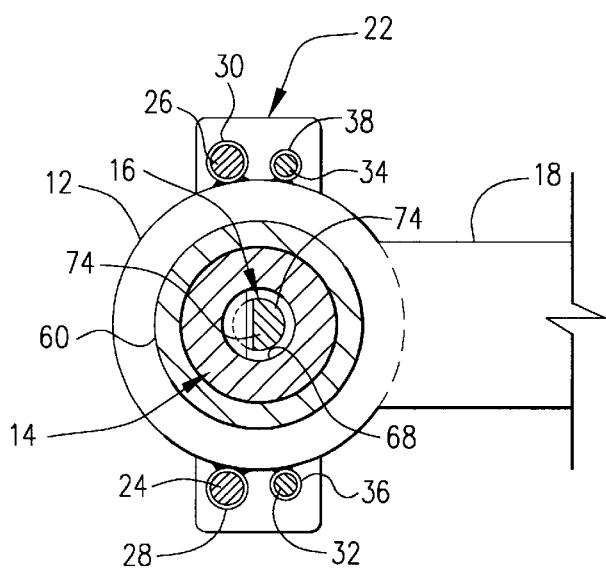
FIG. 6 is a cross-sectional view taken along line 6—6 of FIG. 5.

As best shown in FIGS. 4–6, the endodontic file 16, which can be any suitable type of rotary file, e.g., a K-file, a reamer, a Headstrom file, etc., includes a flexible shaft 69 having a plurality of cutting edges 70 formed thereon and a handle 72 attached to the flexible shaft 69. The handle 72 is elongated and includes an elongated portion 74 having the cross-sectional shape of a straight line segment of a circle. The end 75 of the elongated portion 74 of the handle 72 includes a peripheral circular groove 77 formed therein which is engaged by the latch assembly 22 as will be described further hereinbelow.

The chuck assembly 14 is comprised of a cylindrical member 60 which is journaled within the head portion 12 of the handpiece 10 by bearings 62 and 64. The partially closed upper end portion 66 of the cylindrical member 60 includes an opening 68 for matingly engaging the elongated portion 74 of the endodontic file 16. As best shown in FIG. 6, the elongated portion 74 of the handle 72 of the endodontic file 16 and the complimentary opening 68 in the cylindrical member 60 both have the cross-sectional shapes of straight line segments of a circle whereby the endodontic instrument 16 is caused to rotate with the cylinder 60 when it is rotated, but the endodontic instrument 16 is free to move axially within the cylinder 60. That is, the endodontic file 16 can move between the upper position as shown in FIG. 4 and the lower position shown in FIG. 5 while it is being rotated. As will now be understood, the length of the portion 74 of the handle 72 which has the cross-sectional shape of a straight line segment of a circle, the length of the chuck assembly 14 and the distance that the latch assembly 22 can be moved are such that the endodontic file 16 can be moved a distance between its upper and lower positions which is sufficient to clean and enlarge the root canals of human teeth. The length of the portion 74 of the handle 72 of the endodontic file 16 is at least greater than about 2 millimeters and generally is in the range of from about 2 to about 20 millimeters.

The cylindrical member 60 includes a bevel gear 76 attached thereto which engages a complimentary bevel gear 78 attached to a shaft 80 which extends through the shank portion 18 of the handpiece 10. As best shown in FIG. 1, the other end of the shaft 80 includes a drive gear 82 engaged by a bevel gear 84 which is in turn connected to the shaft 86 of a rotary drive 88, e.g., a selectively reversible electric or air motor. As will be understood, the rotary drive 88 causes the cylindrical member 60 and the endodontic file 16 to rotate in a selected direction by way of the gears 82 and 84, the shaft 80 and the gears 76 and 78.

Figure 7:
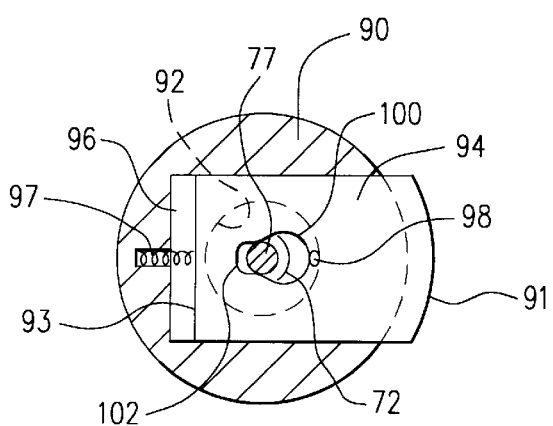
FIG. 7 is a cross-sectional view taken along line 7—7 of FIG. 4.

The latch assembly 22 is comprised of a housing member 90 having a central opening 92 formed therein. A latch member 94 is slidably disposed within the housing member 90 and across the opening 92. As best shown in FIGS. 4 and 7, an end portion 91 of the latch member 94 extends outside of the housing member 90 so that the latch member 94 can be moved within the housing member 90 by manually pushing the end portion 91 into the housing member 90. The other end portion 93 of the latch member 94 extends into a slot 96 in the housing member 90 which contains a spring 97 or other biasing means whereby the latch member 94 is constantly urged in a direction towards the end portion 91 thereof. A stop member 98, such as a pin or screw, prevents the latch member 94 from sliding out of the housing member 90. As best shown in FIG. 7, the latch member 94 has a circular opening 100 formed therein through which the end 75 of the elongated portion 74 of the endodontic file 16 can be inserted when the end portion 91 of the latch member 94 is pushed into the housing 90. A slot 102 (shown in FIG. 7) communicated with the circular opening 100 is also formed in the latch member 94 which slides into the complimentary peripheral circular groove 77 in the end 75 of the elongated portion 74 of the endodontic instrument 16 when the latch member 94 is released and the end portion 91 thereof is moved back out of the housing 90 by the spring 97 as shown in FIGS. 4 and 7.

When the slot 102 is engaged with the peripheral circular groove 77 of the endodontic file 16, the endodontic file 16 is held by the latch assembly 22, but the endodontic file 16 is free to be rotated by the chuck assembly 14. Further, as described above, the movement of the latch assembly 22 towards or away from the chuck assembly 14 by the longitudinal drive 40 simultaneously advances or retracts the endodontic file 16. The endodontic file 16 can be rotated in either the clockwise or counterclockwise direction by the chuck assembly 14, or it can be stationary, while being advanced or retracted.

Thus, in operation of the handpiece 10 illustrated in FIGS. 1–7, the endodontic file 16 is latched into the latching assembly 22 by manually pushing the end portion 91 of the latch member 94 into the housing member 90 and inserting the end 75 of the endodontic file 16 through the cylindrical member 60 of the chuck assembly 14 and through the circular opening 100 of the latch member 94. The latch member 94 is then released so that the slot 102 thereof slides into the peripheral circular groove 77 of the file 16 and is retained in that position by the spring 97. Thereafter, the rotary drive 88 is activated so that the chuck assembly 14 and the endodontic file 16 are rotated in a selected direction at a preselected speed, e.g., a speed in the range of from about 30 rpm to about 3,000 rpm. The rotary drive 54 is then activated in a counterclockwise direction whereby the longitudinal drive 40 pushes the flexible rods 32 and 34 and the latching assembly 22 to a position away from the chuck assembly 14 as shown in FIGS. 1 and 4. The endodontic file 16 and handpiece 10 are next positioned whereby the endodontic file will enter a root canal to be cleaned and enlarged. The rotary drive 54 is again activated whereby the endodontic file 16 is advanced into and retracted from the root canal at controlled rates so that the endodontic file does not become excessively loaded while the root canal is being cleaned and enlarged. That is, the controlled rates at which the endodontic file 16 is advanced into and retracted from the root canal are rates which prevent the file 16 from becoming excessively loaded while moving through the root canal. Generally, the rates at which the endodontic file is advanced into and retracted from a root canal are in the range of from about 0.001 to about 1 millimeter per revolution of the endodontic file 16.

The operation of one or both of the rotary drives 54 and 88 can be controlled by one or more electronic control devices whereby the endodontic file 16 is rotated at a preselected rate and in a preselected direction while the file is being advanced and retracted at controlled rates. Preferably, an electronic control device is utilized which includes a computer that operates both of the rotary drives 54 and 88 in accordance with a predetermined program whereby the endodontic file 16 is advanced and retracted into and from the root canal while being rotated clockwise or counterclockwise in preselected sequences. For example, the computer program can cause the endodontic file 16 to be successively rotated in a clockwise direction while the file is advanced into an uncut portion of a root canal followed by being rotated in a clockwise or counterclockwise direction while the file is being retracted from that portion of the root canal, the rotations of the file being at preselected speeds and the advances and retractions of the file being at controlled rates whereby the endodontic file does not become excessively loaded while the root canal is being cleaned and enlarged.

The present invention, therefore, is well adapted to meet the needs recited above and to carry out the objects and attain the ends and advantages mentioned as well as those inherent therein. While numerous changes can be made in the construction and arrangement of the parts of the handpiece and endodontic file as well as in the method steps of using the handpiece and their arrangement, such changes are encompassed within the spirit of this invention as defined by the appended claims.

What is claimed is:

1. In a rotary handpiece for cleaning and enlarging a root canal of a tooth having a rotary drive connected to a chuck assembly for rotating an endodontic file disposed in the chuck assembly, the improvement which comprises:
   a latch assembly for holding said endodontic file while allowing said chuck assembly to rotate said file about its axis, said latch assembly being movably attached to said handpiece and positioned adjacent to said chuck assembly whereby when said handpiece and said endodontic file are positioned so that said file will enter said root canal and said latch assembly is moved towards or away from said chuck assembly, said endodontic file is advanced into or retracted from said root canal; and
   means attached to said handpiece and to said latch assembly for moving said latch assembly toward and away from said chuck assembly and thereby advancing and retracting said endodontic file at controlled rates so that said file does not become excessively loaded while said root canal is being cleaned and enlarged.

2. The handpiece of claim 1 wherein said means for moving said latch assembly towards and away from said handpiece comprise:
   at least one flexible rod attached to said latch assembly at one end for pulling said latch assembly towards said chuck assembly and pushing said latch assembly away from said chuck assembly;
   a longitudinal drive connected to the other end of said flexible rod and to said handpiece for pulling and pushing said rod; and
   a guide tube for containing and guiding said flexible rod attached to said handpiece.

3. The handpiece of claim 2 wherein two flexible rods are attached to said latch assembly and to said longitudinal drive and two guide tubes are attached to said handpiece for containing and guiding said flexible rods.

4. The handpiece of claim 2 wherein said longitudinal drive comprises:
   a threaded shaft rotatably connected to said handpiece;
   a threaded follower threadedly engaged on said shaft which moves longitudinally on said shaft when said shaft is rotated, said follower being connected to said flexible rod; and
   a rotary drive connected to said threaded shaft for rotating said shaft.

5. The handpiece of claim 4 wherein said rotary drive connected to said threaded shaft is selectively rotatable in either a clockwise or counterclockwise direction.

6. The handpiece of claim 4 wherein said rotary drive connected to said threaded shaft is a second independent rotary drive from said rotary drive which rotates said chuck assembly.

7. The handpiece of claim 6 wherein the operation of said second rotary drive is controlled by an electronic control device.

8. The handpiece of claim 6 wherein the operation of said rotary drive which drives said chuck assembly and said second rotary drive are controlled by an electronic control device comprising a computer.

9. The handpiece of claim 1 wherein said latch assembly is movably attached to said handpiece by a guide rod which is attached to said latch assembly and disposed within a guide tube attached to said handpiece.

10. The handpiece of claim 1 wherein said latch assembly comprises:
    a housing member;
    a latch member slidably disposed in said housing member, said latch member having an opening therein through which the end of said endodontic file extends and having a slot therein which slides into a corresponding peripheral groove in said endodontic file and holds said file; and
    means attached to said housing and to said latch member for biasing said latch member in a direction whereby said slot is constantly urged into said groove.

11. A method of cleaning and enlarging the root canal of a tooth utilizing a rotary endodontic file comprising the steps of:
    (a) latching said endodontic file to a handpiece having a chuck assembly for rotating said file and a latch assembly for holding said file while allowing said chuck assembly to rotate said file about its axis, said latch assembly being selectively movable towards or away from said chuck assembly whereby said file is advanced or retracted;
    (b) positioning said handpiece with said endodontic file positioned to enter said root canal;
    (c) rotating said endodontic file at a preselected speed; and
    (d) advancing and retracting said endodontic file into and from said root canal in a manner and at preselected controlled rates whereby said file does not become excessively loaded while said root canal is being cleaned and enlarged.

12. The method of claim 11 wherein said endodontic file is rotated in accordance with step (c) at a speed in the range of from about 30 rpm to about 3,000 rpm.

13. The method of claim 11 wherein said controlled rates at which said endodontic file is advanced and retracted in accordance with step (d) are rates in the range of from about 0.001 to about 1 millimeter per revolution of said endodontic file.

14. The method of claim 11 wherein said chuck assembly is rotated by a first rotary drive and said latch assembly is moved by a second rotary drive.

15. The method of claim 14 wherein said first and second rotary drives are selectively rotatable in either a clockwise or counterclockwise direction.

16. The method of claim 15 wherein the operation of said second rotary drive is controlled by an electronic control device.

17. The method of claim 15 wherein the operations of said first and second rotary drives are controlled by an electronic control device comprising a computer.

18. The method of claim 11 wherein said endodontic file is rotated in accordance with step (c) in a clockwise direction or a counterclockwise direction.

19. The method of claim 11 wherein said endodontic file is rotated in accordance with step (c) whereby said file is successively rotated in a clockwise direction followed by being rotated in a counterclockwise direction.

20. The method of claim 11 wherein said endodontic file is advanced and retracted in accordance with step (d) whereby said file is successively advanced into an uncut portion of said root canal followed by being retracted from said portion of said root canal.

* * * * *